United States Patent
Ohno et al.

(10) Patent No.: US 9,045,503 B2
(45) Date of Patent: Jun. 2, 2015

(54) METHOD FOR PRODUCING MONOSILANE AND TETRAALKOXYSILANE

(75) Inventors: Hiromoto Ohno, Tokyo (JP); Toshio Ohi, Tokyo (JP); Haruaki Ito, Tokyo (JP); Fanil Makhmutov, Moscow (RU)

(73) Assignee: SHOWA DENKO K.K., Tokyo (JP)

( * ) Notice: Subject to any disclaimer, the term of this patent is extended or adjusted under 35 U.S.C. 154(b) by 276 days.

(21) Appl. No.: 13/509,118

(22) PCT Filed: Nov. 24, 2010

(86) PCT No.: PCT/JP2010/070883
§ 371 (c)(1), (2), (4) Date: May 10, 2012

(87) PCT Pub. No.: WO2011/065359
PCT Pub. Date: Jun. 3, 2011

(65) Prior Publication Data
US 2012/0226064 A1  Sep. 6, 2012

(30) Foreign Application Priority Data
Nov. 25, 2009 (JP) ................................. 2009-267094

(51) Int. Cl.
| | | |
|---|---|---|
| C07F 7/08 | (2006.01) | |
| C07F 7/04 | (2006.01) | |
| B01J 27/16 | (2006.01) | |
| B01J 27/188 | (2006.01) | |
| C01B 33/04 | (2006.01) | |
| B01J 37/02 | (2006.01) | |
| B01J 37/03 | (2006.01) | |
| B01J 23/28 | (2006.01) | |
| B01J 23/30 | (2006.01) | |
| B01J 27/19 | (2006.01) | |
| B01J 35/08 | (2006.01) | |
| B01J 35/10 | (2006.01) | |
| B01J 21/06 | (2006.01) | |

(52) U.S. Cl.
CPC ............... *C07F 7/045* (2013.01); *B01J 21/063* (2013.01); *B01J 27/16* (2013.01); *B01J 27/188* (2013.01); *C01B 33/04* (2013.01); *B01J 37/0238* (2013.01); *B01J 37/031* (2013.01); *B01J 37/033* (2013.01); *B01J 23/28* (2013.01); *B01J 23/30* (2013.01); *B01J 27/19* (2013.01); *B01J 35/08* (2013.01); *B01J 35/1014* (2013.01); *B01J 37/0201* (2013.01); *C01B 33/043* (2013.01); *C01B 33/046* (2013.01)

(58) Field of Classification Search
CPC ............................. C07F 7/188; B01J 2531/48
USPC .......................... 556/469, 470; 502/121, 182
See application file for complete search history.

(56) References Cited

U.S. PATENT DOCUMENTS

| | | | |
|---|---|---|---|
| 4,016,188 A | | 4/1977 | Kötzsch et al. |
| 4,959,200 A | * | 9/1990 | Inaba et al. .................... 423/347 |
| 5,608,096 A | * | 3/1997 | Katsoulis et al. ............. 556/462 |
| 2009/0209796 A1 | * | 8/2009 | Hibi .............................. 585/467 |

FOREIGN PATENT DOCUMENTS

| | | |
|---|---|---|
| JP | 63-210011 A | 8/1988 |
| JP | 63-210012 A | 8/1988 |
| JP | 2001-19418 A | 1/2001 |
| JP | 2002-69078 A | 3/2002 |
| WO | 2008/042445 A2 | 4/2008 |
| WO | 2010/050579 A1 | 5/2010 |

OTHER PUBLICATIONS

International Search Report for PCT/JP2010/070883 dated Feb. 8, 2011.

* cited by examiner

*Primary Examiner* — Sudhakar Katakam
*Assistant Examiner* — Pancham Bakshi
(74) *Attorney, Agent, or Firm* — Sughrue Mion, PLLC

(57) ABSTRACT

The present invention relates to a method for producing monosilane and tetraalkoxysilane comprising subjecting alkoxysilane represented by formula (1)

$$H_nSi(OR)_{4-n} \qquad (1)$$

wherein R represents alkyl group having 1 to 6 carbon atoms and n represents an integer of from 1 to 3, to disproportionation reaction in a gaseous phase in the presence of an inorganic phosphate or a catalyst having a specific chemical structure based on a heteropolyacid salt structure. In the production method of the present invention, separation from the solvent can be carried out easily, the reaction proceeds quickly and the conversion rate of the starting materials is high.

2 Claims, No Drawings

METHOD FOR PRODUCING MONOSILANE AND TETRAALKOXYSILANE

TECHNICAL FIELD

The present invention relates to a method for producing monosilane and tetraalkoxysilane by disproportionation reaction of alkoxysilane.

BACKGROUND ART

Monosilane is useful as a volatile silicone material having high purity, and has been widely used for producing solar cells, semiconductors, amorphous photosensitive silicone materials and various ceramic materials.

Various methods for producing monosilane have been known to date. A method using reaction between magnesium silicide and acid or ammonium bromide, a method by reducing silicon chloride using $LiAlH_4$, a method by reducing silicon tetrafluoride using $CaH_2$ and a method by disproportionation reaction of alkoxysilane have been known.

Trialkoxysilane is generally used as a starting material in the disproportionation reaction of alkoxysilane, and monosilane and tetraalkoxysilane are produced according to the formula as follows:

$$4HSi(OR)_3 \rightarrow SiH_4 + 3Si(OR)_4 \qquad \text{[Chem. 1]}$$

Like monosilane, tetraalkoxysilane is a useful chemical substance as a pure silicon precursor material for producing various silicon compounds for optical fibers, photomasks and IC sealing materials.

Triethoxysilane and trimethoxysilane are used as a starting material in the above-mentioned disproportionation reaction and tetraethoxysilane and tetramethoxysilane are produced at the same time as monosilane, respectively, as shown in the following formulae.

$$4HSi(OMe)_3 \rightarrow SiH_4 + 3Si(OMe)_4$$

$$4HSi(OEt)_3 \rightarrow SiH_4 + 3Si(OEt)_4 \qquad \text{[Chem. 2]}$$

When the above reaction is conducted, metal sodium can be used as a catalyst of the disproportionation reaction. However, the yield is low in the reaction and therefore the method was not practically useful.

Patent Document 1 (U.S. Pat. No. 4,016,188) discloses a method using alkali metal alkoxide or alkali metal silicate as a catalyst. However, the reaction in a liquid phase is too slow such that the reaction time exceeds ten hours, and therefore the method is not suitable for industrial production.

Patent Document 2 (JP-A-2001-19418) discloses a method for producing monosilane and tetraalkoxysilane by disproportionation of alkoxysilane represented by formula $H_nSi(OR)_{4-n}$ wherein n is 1, 2 or 3 and R represents alkyl group or cycloalkyl group, comprising (i) a reaction step of obtaining monosilane and tetraalkoxysilane by disproportionation of alkoxysilane in a solvent in the presence of a catalyst, (ii) a step of extracting part of the solvent containing a catalyst and tetraalkoxysilane from the reaction step, and (iii) a step of separating part or all of the tetraalkoxysilane by distilling the extracted solvent containing a catalyst and tetraalkoxysilane. However, the method also employs disproportionation reaction in a solution and has a problem of difficulties in separation from the solvent and a problem of insufficient reaction rate.

Patent document 3 (WO 2008/042445 pamphlet) discloses a method for producing monosilane and tetramethoxysilane by disproportionation of trimethoxysilane on a potassium fluoride (KF) loaded alumina catalyst. Although this method has no problem with a separation of the catalyst and the like from the reaction products, conversion of trimethoxysilane is not sufficiently high.

PRIOR ART DOCUMENTS

Patent Documents

Patent Document 1: U.S. Pat. No. 4,016,188
Patent Document 2: JP-A-2001-19418
Patent Document 3: WO 2008/042445 pamphlet

DISCLOSURE OF THE INVENTION

Problem to be Solved by the Invention

An objective of the present invention is to provide a method to solve problems as mentioned above that separation from the solvent is difficult, the reaction is too slow and not suitable for industrial production and the conversion of the material is low in a method for producing monosilane and tetraalkoxysilane by disproportionation reaction of alkoxysilane.

Means to Solve the Problems

As a result of intensive studies to solve the above problems in the conventional art, the present inventors have found that the above problems can be solved by disproportionation reaction of alkoxysilane represented by formula (1)

[Chem. 3]

$$H_nSi(OR)_{4-n} \qquad (1)$$

wherein R represents alkyl group having 1 to 6 carbon atoms and n represents an integer of from 1 to 3, in a gaseous phase in the presence of a catalyst having specific chemical structure.

That is, the present invention relates to the following issues:

[1] A method for producing monosilane and tetraalkoxysilane comprising subjecting alkoxysilane represented by formula (1)

[Chem. 4]

$$H_nSi(OR)_{4-n} \qquad (1)$$

wherein R represents alkyl group having 1 to 6 carbon atoms and n represents an integer of from 1 to 3, to disproportionation reaction in a gaseous phase in the presence of a catalyst, which is characterized by use of at least one kind of catalysts selected from a group of compounds represented by below formulae (I) to (V):

[Chem. 5]

$$(M^I{}_2O)z(MO_2)(P_2O_5)x(H_2O)y \qquad (I)$$

wherein M represents any of Zr, Ti, Sn or Si; $M^I$ represents any of hydrogen atom, $NH_4$ or alkali metal; x is 0.5 to 4.5, y is 0.15 to 6.5 and z is 0.15 to 3.5;

[Chem. 6]

$$(MO_2)(P_2O_5)x(H_2O)y \qquad (II)$$

wherein M represents any of Zr, Ti, Sn or Si; x is 0.5 to 4.5 and y is 0.15 to 6.5;

[Chem. 7]

$$(M^I{}_2O)z(MO_2)(P_2O_5)x \qquad (III)$$

wherein M represents any of Zr, Ti, Sn or Si; $M^I$ represents any of hydrogen atom, $NH_4$ or alkali metal; x is 0.5 to 4.5 and z is 0.15 to 3.5;

[Chem. 8]

$$M^I_m[M^{II}_n M^{III}_k O_j] \quad (IV)$$

wherein $M^I$ represents any of hydrogen atom, $NH_4$ or alkali metal; $M^{II}$ represents P(V) or As (V); $M^{III}$ represents W(VI) or Mo (VI); n is an integer of from 1 to 3; k is any of 6, 12, 18 or 24; j is any of 24, 40 or 42 and m is an integer determined by the formula: 2j-5n-6k;

[Chem. 9]

$$M^I_m[M^{IV}_n M^{III}_k O_j] \quad (V)$$

wherein $M^I$ represents any of hydrogen atom, $NH_4$ or alkali metal; $M^{IV}$ represents any of Si(IV), Ge(IV), Ti(IV) or Ce(IV); $M^{III}$ represents W(VI) or Mo(VI); n is an integer of from 1 to 3; k is any of 6, 12, 18 or 24; j is any of 24, 40 or 42 and m is an integer determined by the formula: 2j-4n-6k.

[2] The method for producing monosilane and tetraalkoxysilane as described in [1] above, using as a catalyst a compound represented by formula (Ia) in which x is 1 and z is 1 in formula (I);

[Chem. 10]

$$(M^I_2O)(MO_2)(P_2O_5)(H_2O)y \quad (Ia)$$

wherein M and $M^I$ have the same meanings as described in [1] above and y is from 0.25 to 4.0.

[3] The method for producing monosilane and tetraalkoxysilane as described in [2] above, wherein M is Zr or Ti.

[4] The method for producing monosilane and tetraalkoxysilane as described in [1] above, using as a catalyst a compound represented by formula (IIa) in which M is Zr and x is 1 in formula (II);

[Chem. 11]

$$(ZrO_2)(P_2O_5)(H_2O)y \quad (IIa)$$

wherein y is 1.0 to 5.0.

[5] The method for producing monosilane and tetraalkoxysilane as described in [4] above, wherein y is 1.3 or 3.

[6] The method for producing monosilane and tetraalkoxysilane as described in [1] above, using as a catalyst a compound represented by formula (IIIa) wherein x is 0.5 and z is 0.5 in formula (III);

[Chem. 12]

$$(M^I_2O)_{0.5}(MO_2)(P_2O_5)_{0.5} \quad (IIIa)$$

wherein M represents Zr or Ti and $M^I$ has the same meaning as described in [1] above.

[7] The method for producing monosilane and tetraalkoxysilane as described in [6] above, using a compound represented by a formula in which $M^I$ is K and M is Ti in formula (IIIa);

[Chem. 13]

$$(K_2O)_{0.5}(TiO_2)(P_2O_5)_{0.5}$$

[8] The method for producing monosilane and tetraalkoxysilane as described in [1] above, using as a catalyst a compound represented by formula (IVa) in which $M^{II}$ is P(V) and n is 1 in formula (IV);

[Chem. 14]

$$M^I_m[PM^{III}_k O_j] \quad (IVa)$$

wherein $M^I$, $M^{III}$, k, j and m have the same meanings as described in [1] above.

[9] The method for producing monosilane and tetraalkoxysilane as described in [1] above, using as a catalyst a compound represented by formula (Va) in which $M^{IV}$ is Si(IV) and n is 1 in formula V;

[Chem. 15]

$$M^I_m[SiM^{III}_k O_j] \quad (Va)$$

wherein $M^I$, $M^{III}$, k, j and m have the same meanings as described in [1] above.

[10] The method for producing monosilane and tetraalkoxysilane as described in [9] above, using a compound represented by a formula in which $M^I$ is K, $M^{III}$ is W(VI), k is 12, j is 40 and m is 4 in formula (Va);

[Chem. 16]

$$K_4[SiW_{12}O_{40}]$$

Effects of the Invention

By subjecting alkoxysilane to reaction in a gaseous phase using a catalyst having a specific chemical structure, the method of the present invention can solve the problems involved in a method for producing monosilane and tetraalkoxysilane by disproportionation of alkoxysilane that separation from a solvent is difficult, the reaction rate is very slow and the conversion of the starting material is low.

Mode for Carrying out the Invention

The method for producing monosilane and tetraalkoxysilane of the present invention is to be described in details below.

The present invention relates to a method for producing monosilane and tetraalkoxysilane, characterized in subjecting alkoxysilane represented by formula (1) to disproportionation reaction in gaseous phase in the presence of a catalyst having a specific chemical structure.

[Chem. 17]

$$H_nSi(OR)_{4-n} \quad (1)$$

In the formula, R represents alkyl group having 1 to 6 carbon atoms and n represents an integer of from 1 to 3.

Examples of alkoxysilane represented by formula (1) as a starting material of the disproportionation reaction in the present invention include monoalkoxysilane, dialkoxysilane and trialkoxysilane. R represents alkyl group having 1 to 6 carbon atoms, and preferably alkyl group having 1 to 2 carbon atoms. Particularly preferred examples of alkoxysilane include monomethoxysilane, dimethoxysilane, trimethoxysilane, monoethoxysilane, diethoxysilane and triethoxysilane. Among these, trimethoxysilane and triethoxysilane are most preferable.

Disproportionation catalyst for the method of the present invention is an inorganic catalyst having a chemical structure based on phosphate or heteropolyacid salt structure.

The first disproportionation catalyst of alkoxysilane of the present invention is selected from a group of inorganic phosphate having the below chemical structure;

[Chem. 18]

$$(M^I_2O)z(MO_2)(P_2O_5)x(H_2O)y, \quad (I)$$

In the formula, M represents any of Zr, Ti, Sn or Si; $M^I$ represents any of hydrogen atom, $NH_4$ or alkali metal; x is from 0.5 to 4.5; y is from 0.15 to 6.5 and z is from 0.15 to 3.5.

There are several methods for preparing the above-mentioned phosphate catalyst composition. A general method is to form a sol of metal oxide selected from Zr, Ti, Sn and Si in an aqueos solution at low temperature by a known appropriate procedure. Examples include a method of hydrolysis of alkoxide and a method of deflocculation of precipitation of metal oxide ($MO_2$) selected from Zr, Ti, Sn or Si by phosphoric acid or alkali. The obtained sol can be stabilized with a phosphoric acid solution and is accumulated by the subsequent heating or alkali treatment. Further, a conventionally known high-temperature heating treatment can be provided to the mixture of the equivalent salt or oxide. Another example is a freezing chemical method including preparation of a catalyst core in an aqueous solution, and low-temperature sublimation and stabilization of the catalyst.

Among the catalysts represented by the above formula (I), preferable are the compounds represented by formula (Ia) wherein x is 1 and z is 1;
[Chem. 19]

$$(M^I_2O)(MO_2)(P_2O_5)(H_2O)y \quad (Ia)$$

In the formula, M and $M^1$ have the same meanings as mentioned above, and y is from 0.25 to 4.0, and particularly preferable are the compounds in which M is Zr or Ti.

The catalyst of this group represents mixed phosphate of monovalent cation and metal selected from Zr, Ti, Sn or Si. Examples of the salts include $K_2Ti(PO_4)_2(H_2O)_{0.3}$, i.e. $(K_2O)(TiO_2)(P_2O_5)(H_2O)_{0.3}$. It can be prepared in a form of half-hydrate by ordinarily anealing the mixture of $TiO_2$ and $KH_2PO_4$ at a molar ratio of 1:2 and 15 mass % of water at high temperature. The mixture is to be heated up to 400° C. while releasing moisture slowly.

The second disproportionation catalyst of alkoxysilane of the present invention is selected from a group of inorganic phosphate having the below chemical structure;
[Chem. 20]

$$(MO_2)(P_2O_5)x(H_2O)y \quad (II)$$

In the formula, M represents any of Zr, Ti, Sn or Si; and x is from 0.5 to 4.5 and y is from 0.15 to 6.5. Among the catalysts represented by the above formula (II), preferable are the compounds represented by formula (IIa) wherein M is Zr and x is 1;
[Chem. 21]

$$(ZrO_2)(P_2O_5)(H_2O)y \quad (IIa)$$

In the formula, y is from 1.5 to 5.0. The compound represented by formula (IIa) is known as zirconium phosphate represented as $Zr(HPO_4)_2 \cdot nH_2O$. Among these, the compound represented by $(ZrO_2)(P_2O_5)(H_2O)_{1.3}$ wherein y is 1.3 and $(ZrO_2)(P_2O_5)(H_2O)_3$ wherein y is 3 are particularly preferable. These compounds can be represented as $Zr(HPO_4)_2 19\ 0.3H_2O$ and $Zr(HPO_4)_2 \cdot 2H_2O$.

The third disproportionation catalyst of alkoxysilane of the present invention is selected from a group of inorganic phosphate having the below chemical structure;
[Chem. 22]

$$(M^I_2O)z(MO_2)(P_2O_5)x \quad (III)$$

In the formula, M represents any of Zr, Ti, Sn or Si. $M^I$ represents any of hydrogen atom, $NH_4$ or alkali metal. x is from 0.5 to 4.5 and z is from 0.15 to 3.5.

Among the catalysts represented by the above formula (III), preferable are compounds represented by formula (IIIa) wherein x is 0.5 and z is 0.5.
[Chem. 23]

$$(M^I_2O)_{0.5}(MO_2)(P_2O_5)_{0.5} \quad (IIIa)$$

In the formula, M represents Zr or Ti. $M^I$ has the same meaning as the above. The compounds represented by formula (IIIa) can be described as $M^I(MO)PO_4$. Among these, particularly preferable is the formula $(K_2O)_{0.5}(TiO_2)(P_2O_5)_{0.5}$ in which $M^I$ is K and M is Ti, i.e. $K(TiO)PO_4$.

The catalyst can be prepared by several appropriate methods. An example of the methods for production is as below:
(a) A colloid solution ($TiO_2$ precursor from titanium tetraalkoxide or oxychloride) is prepared.

(b) The sol solution is mixed with dilute aqueous solution of phosphoric acid and potassium carbonate.
(c) $K(TiO)PO_4$ colloid solution obtained by the above mixture is applied onto a γ-alumina support and subject to heat treatment at temperature of 500 to 550° C. The formation of $K(TiO)PO_4$ is confirmed by analyzing the part coated with the solution.

The fourth disproportionation catalyst of alkoxysilane of the present invention is selected from a group of compounds having the below chemical structure.
[Chem. 24]

$$M^I_m[M^{II}_nM^{III}_kO_j] \quad (IV)$$

In the formula, $M^I$ represents any of hydrogen atom, $NH_4$ or alkali metal; $M^{II}$ represents P(V) or As(V); $M^{III}$ represents W(VI) or Mo(VI); n is an integer of from 1 to 3; k is 6, 12, 18 or 24; j is 24, 40 or 42; and m is an integer determined by the formula: 2j-5n-6k.

The catalyst of the group is an anionic complex compound, i.e. a heteropoly acid having hexavalent ligand around element $M^{II}$ which forms a complex in the internal coordinate area. The catalyst represents heteropoly acid having a monovalent cation or salt thereof, includes pentavalent phosphorus and arsenic as elements forming a complex, and has a molybdenum salt or tungsten salt as an anionic ligand in the internal coordinate area.

Among the catalysts represented by the above formula (IV), preferable are the compounds represented by formula (IVa) wherein $M^{II}$ is P(V) and n is 1.
[Chem. 25]

$$M^I_m[PM^{III}_kO_j] \quad (IVa)$$

In the formula, $M^I$, $M^{III}$, k, j and m have the same meanings as mentioned above.

Examples of catalysts of this kind include $K_3[PMo_{12}O_{40}]$, $H_7[PMo_{12}O_{42}]$, $H_3[PMo_{12}O_{40}]$ and $H_7[PW_{12}O_{42}]$.

The fifth disproportionation catalyst of alkoxysilane of the present invention is selected from a group of compounds having the below chemical structure.
[Chem. 26]

$$M^I_m[M^{IV}_nM^{III}_kO_j] \quad (V)$$

In the above formula (V), $M^I$ represents any of hydrogen atom, $NH_4$ or alkali metal; $M^{IV}$ represents Si(IV), Ge(IV), Ti(IV) or Ce(IV); $M^{III}$ represents W(VI) or Mo(VI); n is an integer of from 1 to 3; k is 6, 12, 18 or 24; j is 24, 40 or 42; and m is an integer determined by the formula: (2j-4n-6k).

Catalysts of this group also relate to heteropoly acid or salt thereof. These catalysts contain Si(IV), Ge(IV), Ti(IV) or Ce(IV) which are quadrivalent metals as an element forming a complex.

Among the catalysts represented by the above formula (V), preferable are the compounds represented by formula (Va) wherein $M^{IV}$ is Si(IV) and n is 1.
[Chem. 27]

$$M^I_m[SiM^{III}_kO_j] \quad (Va)$$

In the formula, $M^I$, $M^{III}$, k, j and m have the same meanings as mentioned above.

Examples of catalyst of this kind include $Na_8[TiMo_6O_{24}]$ and $K_4[SiW_{12}O_{40}]$. $K_4[SiW_{12}O_{40}]$ is particularly preferable.

Catalyst represented by the above formula (IV) or (V) can be prepared by an appropriate method known as a method for preparation of each heteropoly acid or salt thereof.

A typical method is reacting molybdenum salt or tungsten salt with phosphoric acid in an acid aqueous solution, followed by drying. The reaction in the case of molybdenum salt is as below:

[Chem. 28]

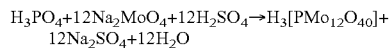

[Chem. 28]

Subsequently, the targeted catalyst is obtained by evaporating moisture partially, impregnating inorganic support with a catalyst solution and subjecting the support to heating treatment. Corresponding heteropoly acid is prepared by a method selected from the two methods which are:
(i) treating the heteropoly acid with metal hydroxide or carbonate slowly, or
(ii) neutralizing the surface of the supported heteropoly acid by cation exchange method.

The catalyst structures of the present invention are used in the solid state in most cases.

They can be used in either form which is a form of solid granulated substance or a form in which a catalyst is supported on an inert inorganic support made of alumina, titania, silica, carbon or other kinds.

The other specific examples of preparation methods of catalyst include a deposition of the catalyst of the present invention on a surface of ion exchange resin. An example of ion exchange resin useful for preparing a supported catalyst of the present invention is a cross-linking cation exchange resin without having a phosphoric acid group.

It is effective to use the thus-obtained catalyst in an amount of at least 0.02 parts by mass to 100 parts by mass of alkoxysilane as a starting material. The catalyst is used in an amount of from 0.02 to 50 parts by mass generally, and preferably in an amount of from 0.1 to 20 parts by mass.

The disproportionation reaction can be performed either in a batch mode or a continuous flow mode. Alkoxysilane used as a starting material and the catalyst do not have high chemical reactivity. Therefore, the process can be carried out without particular limitations on the material of the apparatus.

Accordingly, various types of reactors can be used in the process and therefore the process can be said to be a catalyst system suitable for an industrial production method.

It is preferable to perform the disproportionation reaction upon heating and under atmospheric pressure. The preferable temperature varies depending on alkoxysilane to be used as a starting material and is generally in a range of from 100 to 200° C.

The reaction pressure of the disproportionation reaction can be set within a range of from 0.2 to 10 atmospheres. Since the reaction is not highly pressure-dependent, it is preferable to perform the process under atmospheric pressure. However, it is known that monosilane as a reaction product is ready to ignite on contact with air. Therefore, to prevent the reaction medium including monosilane from igniting on exposure to air, it is preferable to perform the reaction under inert gas atmosphere such as nitrogen or argon.

Monosilane generated by the reaction has a boiling point of −111.9° C. and collected in the form of gas after being taken out from the reactor. When the reaction is performed in a batch method, tetraalkoxysilane remains in the reactor. When a reactor of a flow method is used, tetraalkoxysilane and unreacted trialkoxysilane pass through the reactor, tetraalkoxysilane is condensed and trialkoxysilane is to be returned to the catalyst reactor. The catalyst used in the present invention is insoluble both in starting materials and a reaction product, and can be used for a long-term operation period.

EXAMPLES

The invention will be described with reference to Examples below, but the invention is not limited thereto.

Comparative Example 1

Active potassium fluoride was prepared by slowly evaporating a solvent of a solution of potassium fluoride and dried methanol (1:13 to 20 parts by mass) under reduced pressure so as to recrystallize potassium fluoride and then drying it while raising the temperature.

It is preferable not only to use the methanol for purification having purity higher than 99.9% which complies with US Pharmacopeia tests by A. C. S. but also to use dry nitrogen atmosphere. In the process of evaporating methanol, the temperature is preferably 25 to 35° C.

The subsequent process of drying in vacuum should be performed at least for 5 to 6 hours within the temperature range of 75 to 120° C.

The alumina having potassium fluoride supported thereon is prepared as follows. 30 g of neutral alumina having a particle diameter of 0.3 to 1.0 mm and 20 g of potassium fluoride prepared by recrystalization as the above are mixed with 200 ml deionized water. A solvent is evaporated at 50 to 60° C. while being lightly deaerated. The remaining product is dried for three hours while being deaerated.

Next, using the product as a catalyst for disproportionation reaction of trimethoxysilane, the process for preparing monosilane and tetraalkoxysilane was performed as follows. 1.0 g of alumina on which potassium fluoride is supported was charged in a reaction tube made of Pyrex (registered trademark) glass provided with an electric furnace and heated to 120° C. The mixture of evaporated trimethoxysilane (flow rate: 3.5 ml/min.) and helium (flow rate: 35 ml/min.) was heated to 120° C. in a preheater and next supplied to a reaction tube to thereby perform disproportionation reaction at 120° C. The reaction mixture in the form of gas taken out from the reaction tube was subjected to gas chromatography (GC) analysis for every 20 minutes.

Ten minutes after the reaction had started, the ratio of unreacted trimethoxysilane, generated monosilane and tetramethoxysilane was substantially constant in the reaction product. Dimethoxysilane and monomethoxysilane were not detected the first one hour after the reaction had started.

The analysis after performing the reaction in a flow reactor system for five hours showed the following results.

That is, the trimethoxysilane conversion was 63%, the yield of monosilane to the supplied trimethoxysilane was 63% (in other words, the yield of monosilane to the converted trimethoxysilane was 100%) and the yield of tetramethoxysilane to the supplied trimethoxysilane was 63% (in other words, the yield of tetramethoxysilane to the converted trimethoxysilane was 100%). No by-product was found by the gas chromatography.

EXAMPLE 1

Hydrated zirconium dioxide sol was treated with 1.0 M/l of $H_3PO_4$ solution at an atom ratio P/Zr as 2.0 and dried at 105° C. until it becomes to a certain weight. The obtained granular product is spherical in shape having a diameter of 0.8 to 1.6 mm and the specific surface area of 35 $m^2/g$. X-ray test showed that the product is amorphous. According to chemical analysis, this product has chemical structure in which x is 1 and y is 3 in the above formula (II). That means, the chemical structure of the obtained product corresponds to the formula: $(ZrO_2)(P_2O_5)(H_2O)_3$. It can be also described as $Zr(HPO_4)_2 \cdot 2H_2O$. The product was filled in a test cell, and preheated at 130° C. for one hour under helium flow before trimethoxysilane was supplied. Thus-obtained product was used as a catalyst for trimethoxysilane disproportionation reaction, and the catalyst activity was evaluated in a similar manner as comparative example 1. Table 1 shows the result.

EXAMPLES 2 to 9

Catalysts of examples 2 to 9 were prepared in accordance with the below method.

Catalyst of example 2: Catalyst of example 1 was treated with a sodium chloride solution for ion exchange, and washed and dried.

Catalyst of example 3: Catalyst of example 1 was titrated with a potassium carbonate $K_2CO_3$ solution, and washed and dried.

Catalyst of example 4: Titanium oxide ($TiO_2$) was mixed with 15 mass % aqueous solution of potassium dihydrogen phosphate ($KH_2PO_4$) at a molar ratio of $TiO_2$:$KH_2PO_4$ as 1:2, and dried with heat until no liquid remains.

Catalyst of example 5: Titanium oxide ($TiO_2$) was treated with a phosphoric acid ($H_3PO_4$) solution and a potassium carbonate ($K_2CO_3$) solution, and the formed $K(TiO)PO_4$ sol was applied on alumina ($\gamma$-$Al_2O_3$).

Catalyst of example 6: Phosphotungstic acid supported on carbon particles,

Catalyst of example 7: Sodium phosphomolybdic acid supported on carbon particles, Catalyst of example 8: Mixture of ammonium phosphotungstic acid powder and alumina pellets, Catalyst of example 9: Mixture of potassium silicotungstic acid powder and alumina pellets.

The above-mentioned catalysts were used as a catalyst for trimethoxysilane disproportionation reaction, and the catalystic activity was evaluated.

The trimethoxysilane disproportionation reaction and analysis of the products thereof was performed in the similar manner as comparative example 1. Each catalyst was filled in a test cell and preheated at the temperature as described in Table 1 for one hour under helium flow before trimethoxysilane was supplied. The results are shown in Table 1.

In examples 1 and 2, reaction products during the first 1 to 1.5 hours showed the production of 2 to 3% of methanol and equivalent amount of dimethylsilanol.

After that period, the result showed that the reaction products were monosilane and tetramethoxysilane only.

As for the experiments of examples 3 to 8, no product other than monosilane and tetramethoxysilane was detected by GC analysis. Accordingly, the selectivity of the process was 100% with respect to the converted trimethoxysilane. No other reaction product such as alcohol and dimer of hexamethoxydisiloxane was found in the reaction mixture.

All the catalysts used are insoluble in the starting materials and reacted products.

No mass decrease of the catalysts was observed during the reaction. No decrease in the catalyst activity was observed during the five-hour reaction, either.

The results in Table 1 show that the catalyst efficiency is high in the present invention. A flow reactor system can be used for these reactions, and the method can be easily applied to the production of monosilane and tetraalkoxysilane on a continuous industrial scale. Tetraalkoxysilane can be recovered as liquid and monosilane can be recovered as gas. Therefore, separation of the two is easy.

TABLE 1

| Example | Catalyst | Pre-heating temp. (° C.) | Conversion of trimethoxysilane (%) |
|---|---|---|---|
| 1 | $Zr(HPO_4)_2 \cdot 2H_2O = (ZrO_2)(P_2O_5)(H_2O)_3$ | 130 | 94 |
| 2 | $(Na_2O)_{0.3} \cdot (ZrO_2)(P_2O_5)(H_2O)_{2.7}$ | 130 | 96 |
| 3 | $(K_2O)_{1.2}(ZrO_2)(P_2O_5)(H_2O)_{1.8}$ | 150 | 90 |
| 4 | $K_2Ti(PO_4)_2(H_2O)_{0.3} = (K_2O)(TiO_2)(P_2O_5)(H_2O)_{0.3}$ | 400 | 87 |
| 5 | $K(TiO)PO_4 = (K_2O)_{0.5}(TiO_2)(P_2O_5)_{0.5}$ | 500-550 | 95 |
| 6 | $H_3[PW_{12}O_{40}]$ | 120 | 93 |
| 7 | $Na_7[PMo_{12}O_{42}]$ | 150 | 84 |
| 8 | $(NH_4)_3[PW_{12}O_{40}]$ | 130 | 86 |
| 9 | $K_4[SiW_{12}O_{40}]$ | 150 | 94 |

EXAMPLES 10 to 15

The disproportionation reaction and the analysis of the products were performed in the same way as in comparative example 1 using the catalysts shown in Table 2 and alkoxysilane.

Regarding the selectivity, the mole percent ratio of tetraalkoxysilane to the total amount of monoalkoxysilane, dialkoxysilane, trialkoxysilane and tetraalkoxysilane was calculated. Other impurities such as alcohol and siloxane dimer were not detected in the reaction products. The results are shown in Table 2.

TABLE 2

| Example | Catalyst | Reaction temp. (° C.) | Type of alkoxysilane as a starting material | Conversion (%)/ Selectivity (%) |
|---|---|---|---|---|
| 10 | $Zr(HPO_4)_2 \cdot 0.3H_2O = (ZrO_2)(P_2O_5)(H_2O)_{1.3}$ | 130 | Trimethoxysilane | 95/100 |
| 11 | $H_3[PW_{12}O_{40}]$ | 130 | Dimethoxysilane | 72/85 |
| 12 | $Zr(HPO_4)_2 \cdot 0.3H_2O = (ZrO_2)(P_2O_5)(H_2O)_{1.3}$ | 120 | Methoxysilane | 98/74 |
| 13 | $Zr(HPO_4)_2 \cdot 0.3H_2O = (ZrO_2)(P_2O_5)(H_2O)_{1.3}$ | 180 | Triethoxysilane | 83/100 |
| 14 | $H_3[PW_{12}O_{40}]$ | 170 | Diethoxysilane | 87/89 |
| 15 | $(NH_4)_3[PW_{12}O_{40}]$ | 170 | Ethoxysilane | 94/66 |

The results in Table 2 show that the catalyst of the present invention has high catalyst efficiency.

The conversion can be improved by making the time of contact between the gaseous reaction mixture and the catalyst in the reactor longer.

The invention claimed is:

1. A method for producing monosilane and tetraalkoxysilane comprising subjecting alkoxysilane represented by formula (1)

$$H_nSi(OR)_{4-n} \quad (1)$$

wherein R represents alkyl group having 1 to 6 carbon atoms and n represents an integer of from 1 to 3, to disproportionation reaction in a gaseous phase in the presence of a catalyst represented by below formula (Ia):

$$(M^I{}_2O)(MO_2)(P_2O_5)(H_2O)y \quad (Ia)$$

wherein M represents any of Zr, Ti, Sn or Si; $M^I$ represents any of hydrogen atom, $NH_4$ or alkali metal; and y is 0.25 to 4.0.

2. The method for producing monosilane and tetraalkoxysilane according to claim 1, wherein M is Zr or Ti.

* * * * *